US00PP36751P2

(12) United States Plant Patent
Elstgeest

(10) Patent No.: US PP36,751 P2
(45) Date of Patent: Jun. 17, 2025

(54) ***PHILODENDRON* PLANT NAMED 'PHELST01'**

(50) Latin Name: *Philodendron bipinnatifidum*
Varietal Denomination: PHELST01

(71) Applicant: Elstgeest Young Plants Holding BV, Rijsenhout (NL)

(72) Inventor: Debbie Elstgeest, Rijsenhout (NL)

(73) Assignee: Elstgeest Young Plants Holding BV, Rijsenhout (NL)

( * ) Notice: Subject to any disclaimer, the term of this patent is extended or adjusted under 35 U.S.C. 154(b) by 0 days.

(21) Appl. No.: 18/831,362

(22) Filed: Dec. 12, 2024

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./381
See application file for complete search history.

*Primary Examiner* — Susan McCormick Ewoldt
*Assistant Examiner* — Zachariah Allan Kay
(74) *Attorney, Agent, or Firm* — Samuel R. McCoy, Jr.

(57) ABSTRACT

'PHELST01' is a distinctive *Philodendron* plant which is characterized by the combination of a compact growth habit with an abundance of dark green, broadly ovate foliage with shallow lobes, foliage that is moderately concave with pendulous foliar lobes, furrowing of the adaxial foliar surface due to the sunken venation, prominent raised venation of the abaxial foliar surface, as well as the uniformity and stability of these characteristics from generation to generation.

3 Drawing Sheets

Latin name of the genus and species: The Latin name of the genus and species of the novel variety disclosed herein is *Philodendron bipinnatifidum.*

Variety denomination: The inventive variety of *Philodendron* disclosed herein has been given the variety denomination 'PHELST01'.

BACKGROUND OF THE INVENTION

Parentage: 'PHELST01' is a spontaneous, naturally-occurring, whole-plant mutation which was discovered growing amongst a cultivated population of unnamed *Philodendron bipinnatifidum* plants (not patented) which was discovered by the inventor in September of 2018 at a commercial greenhouse in Rijsenhout, the Netherlands. The mutation was first noted for its unique, dark green leaves relative to those of the parent plant and was subsequently isolated for further evaluation in order to confirm the distinctness and stability of the characteristics first observed. Upon confirmation of distinctness and stability, the new *Philodendron* plant was selected for commercialization and given the name 'PHELST01'.

Asexual Reproduction: Asexual reproduction of the new cultivar 'PHELST01', by way of meristematic tissue culture micropropagation, was first initiated in March of 2019, at tissue culture laboratory in Rijsenhout, the Netherlands. Through seven subsequent generations, the unique features of this cultivar have proven to be stable and true to type.

SUMMARY OF THE INVENTION

The cultivar 'PHELST01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PHELST01'. These characteristics in combination distinguish 'PHELST01' as a new and distinct *Philodendron* cultivar:

1. *Philodendron* 'PHELST01' exhibits a relatively compact growth habit with an abundance of glossy, dark green foliage; and
2. *Philodendron* 'PHELST01' exhibits tough, durable foliage borne on sturdy, upright petioles; and
3. *Philodendron* 'PHELST01' exhibits broadly ovate, moderately concave foliage with shallow, pendulous lobes; and
4. *Philodendron* 'PHELST01' exhibits furrowing of the adaxial foliar surface due to the sunken venation and prominent raised venation of the abaxial foliar surface.

BOTANICAL DESCRIPTION OF THE PLANT

Figure 1:
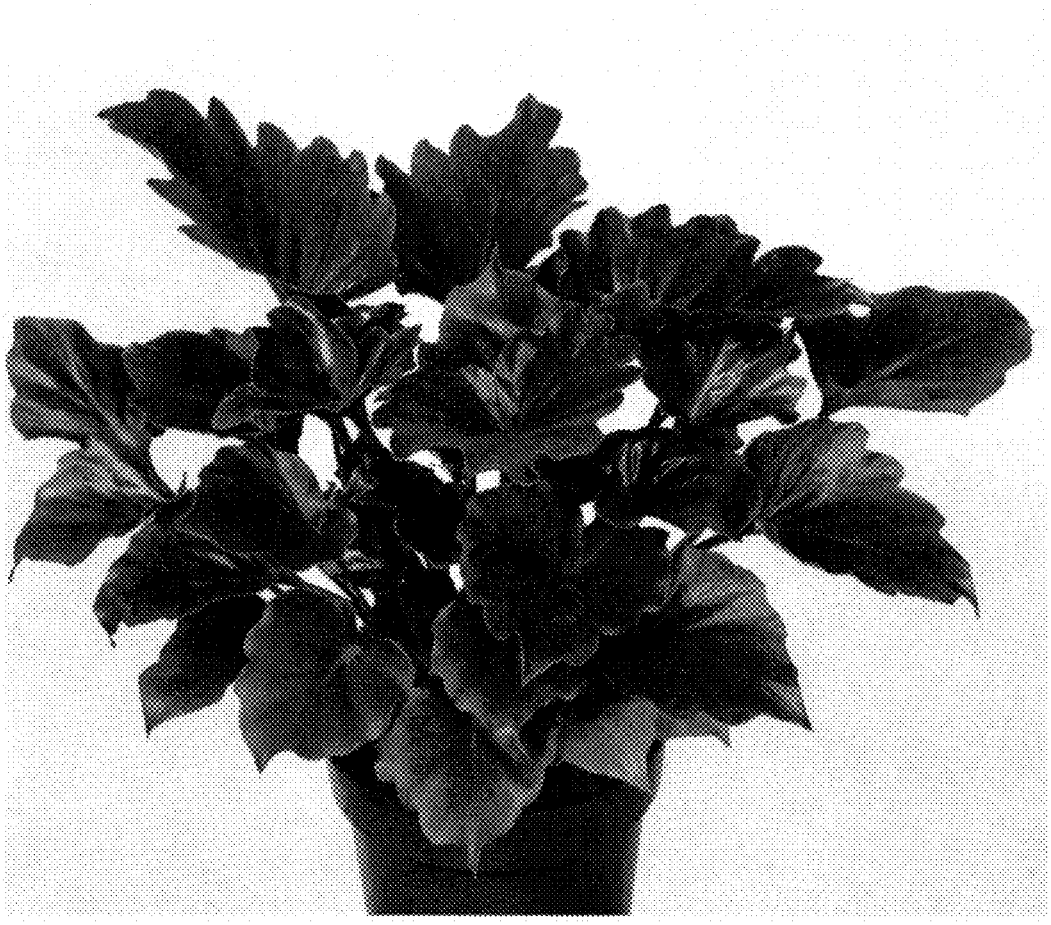
FIG. 1 illustrates, as nearly true as it is reasonably possible to make the same in color photographs of this type, an exemplary plant of 'PHELST01' grown in a commercial greenhouse in Rijsenhout, the Netherlands. This plant is approximately 12 months old in a 13 cm container.
Figure 2:
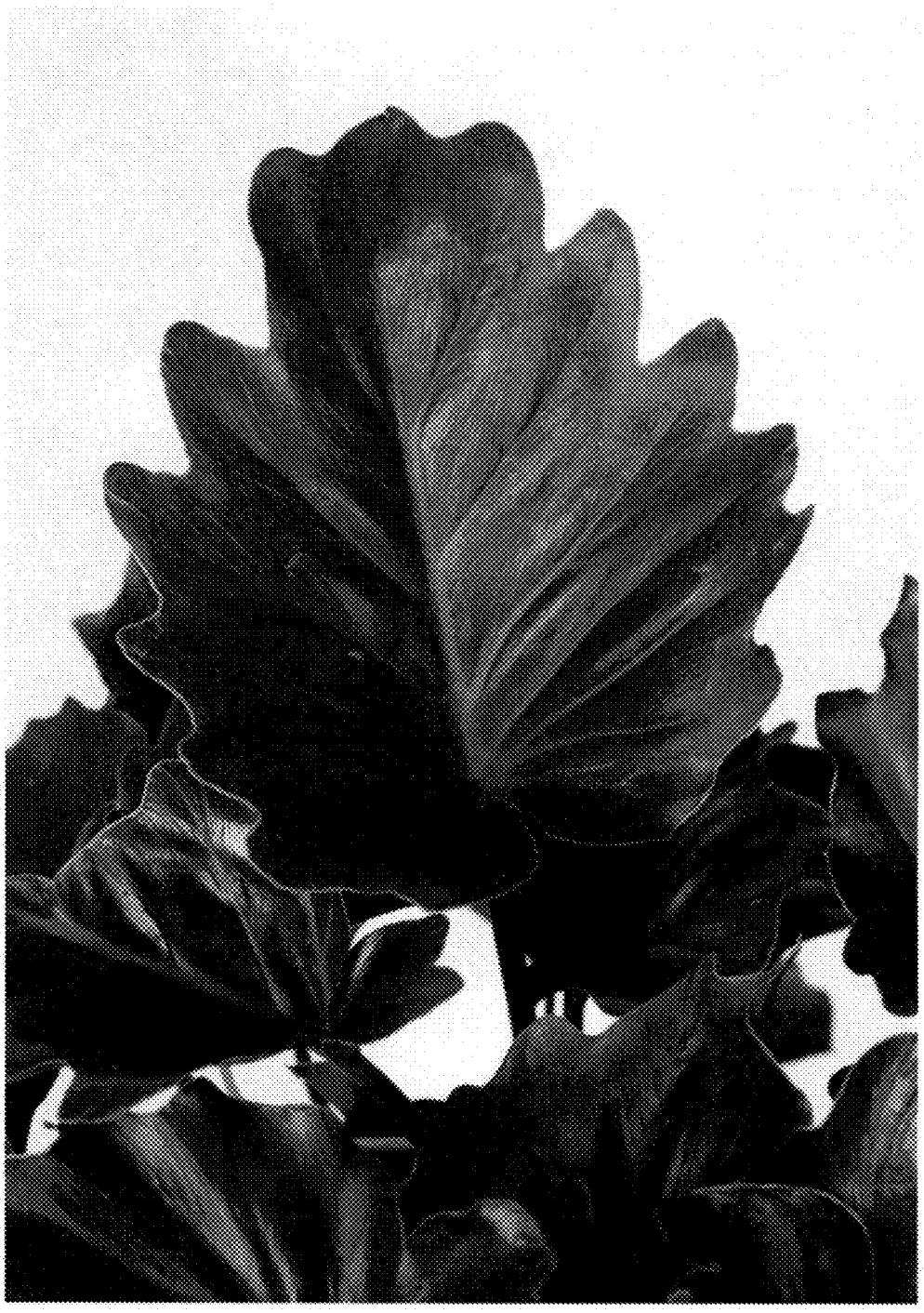
FIG. 2 illustrates, as nearly true as it is reasonably possible to make the same in color photographs of this type, the adaxial surface of the mature foliage of 'PHELST01'.
Figure 3:
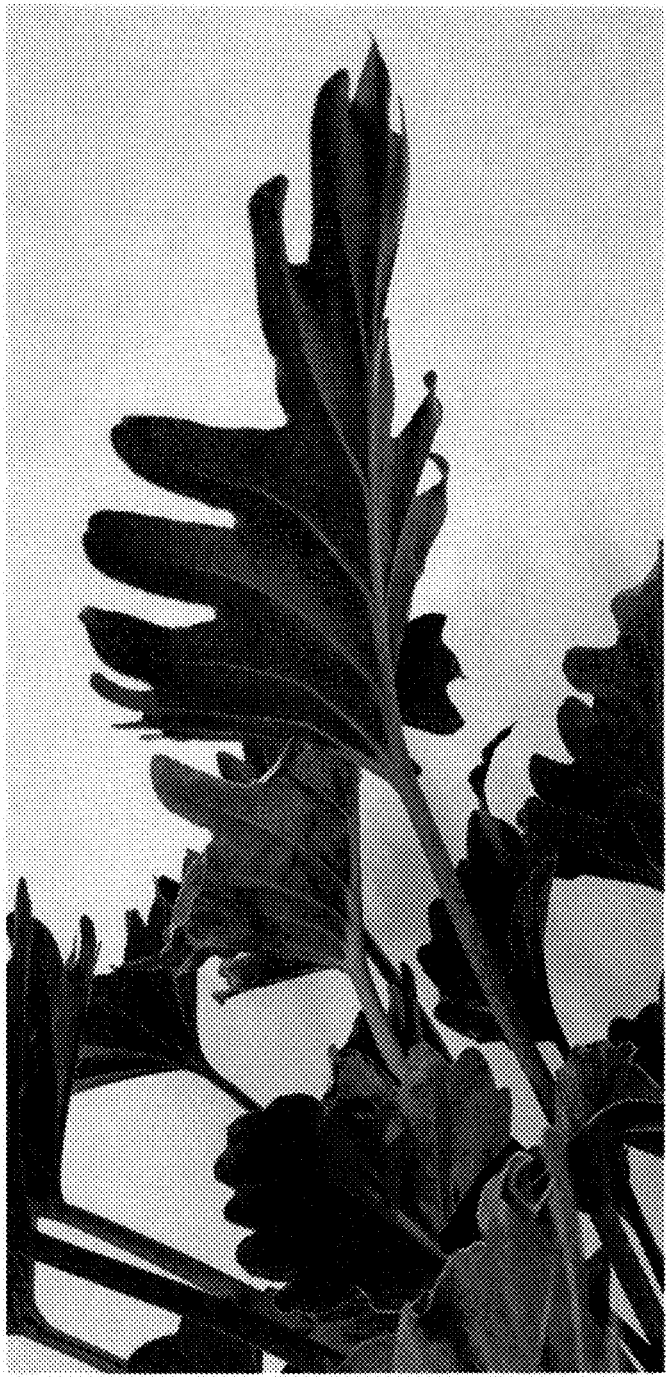
FIG. 3 illustrates, as nearly true as it is reasonably possible to make the same in color photographs of this type, the foliar lobes and abaxial foliar surface of 'PHELST01'.

The following observations and measurements, made in December of 2023, describe averages from a sample set of six 12-month-old 'PHELST01' plants grown in 17 cm nursery containers at a greenhouse in Rijsenhout, the Netherlands. Plants were produced using conventional greenhouse production protocols for *Philodendron* sp. which consisted of growing plants under shade, watering with drip irrigation, and producing plants without supplemental fertilizer, chemical pest measures, or photoperiodic treatments.

Those skilled in the art will appreciate that certain characteristics will vary with older or, conversely, with younger plants. 'PHELST01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'PHELST01' and a comparison with the parent plant and most similar commercial cultivar are provided below.

Plant description:

*Growth habit*.—Broad spreading to upright herbaceous perennial with foliage growth from basal shoots.

*Plant shape*.—Broadly obovate to flattened globular.

*Height from soil level to top of foliar plane*.—28.4 cm.

*Plant spread*.—46.6 cm.

*Number of basal shoots per plant*.—7.

*Plant vigor*.—Moderately vigorous.

*Propagation*.—Type — Asexual propagation is accomplished by way of meristematic tissue culture micropropagation. Time to initiate rooting — Approximately 8 weeks at 21 degrees Celsius. Time to produce a rooted cutting — Approximately 16 weeks are needed to produce a marketable plant in a 14 cm nursery container.

*Disease and pest resistance or susceptibility*.—Neither susceptibility nor resistance to pests and diseases common to either *Philodendron bipinnatifidum* have been observed.

*Environmental tolerances*.—Adapt to temperatures as low as 5 degrees Celsius and at least as high as 40 degrees Celsius; moderate tolerance to rain; low to moderate tolerance to wind.

Roots:

*General*.—Moderately dense, moderately branched rooting; roots are fleshy and non-fibrous.

*Distribution in the soil profile*.—Shallow to moderately deep.

*Texture*.—Smooth, with fine lateral roots.

Foliage:

*Quantity*.—7 leaves per shoot.

*Arrangement*.—Alternate.

*Attachment*.—Petiolate.

*Division*.—Simple.

*Lamina*.—Shape — Broad ovate; lobed. Lobes — Apex — Obtuse. Depth of sinuses — Shallow. Sinus orientation — Divergent. Length — 15.5 cm, excluding the petiole. Width — 13.2 cm. Apex — Acute, with a short mucronate tip. Base — Hastate, lobes touching to slightly overlapping. Aspect — Moderately concave; foliar lobes and apex are pendulous. Margins — Entire margins with strong, coarse undulation. Texture and luster, adaxial surface — Smooth yet slightly furrowed by the venation, glabrous, and slightly to moderately glossy. Texture and luster, abaxial surface — Smooth with pronounced venation, glabrous, and moderately glossy. Color — Juvenile foliage, adaxial surface — Green, nearest to a blend of RHS 137B and 143A. Juvenile foliage, abaxial surface — Green, nearest to a blend of RHS 137B and 144A. Mature foliage, adaxial surface — Green to yellow-green, nearest to a blend of RHS 137A, 147A, and 139A. Mature foliage, abaxial surface — Green to yellow-green, nearest to a blend of RHS 143A and 146A. Venation — Pattern — Pinnate. Color, adaxial surfaces — Green, nearest to RHS 137A. Color, abaxial surface — Yellow-green, nearest to a mixture of RHS 144A and 144B.

*Petiole*.—Attitude — Upright and outward. Strength — Moderately strong. Aspect — Subterete; adaxially flattened and abaxially rounded. Length — 17.8 cm. Width — 0.7 cm at the point of attachment to the lamina. Texture and luster, adaxial surface — Smooth, glabrous and moderately glossy. Texture and luster, abaxial surface — Smooth, glabrous and moderately glossy. Color, adaxial surface — Green, nearest to a blend of RHS 137B and 143A. Color, abaxial surface — Yellow-green, nearest to RHS 144A.

*Petiole wing*.—General — A thin flange of tissue, present at the base of petioles. Shape — Deltoid. Length — 12.2 cm. Width — 0.7 cm. Margin — Entire, with little to no undulation. Texture and luster — Smooth, glabrous and somewhat glossy. Adaxial color — Yellow-green, nearest to RHS 145B, and margined with a translucent yellow-green, nearest to RHS 145D; finely veined green, nearest to RHS 143B and 143C. Abaxial color — Yellow-green, nearest to RHS 144A, and margined with a translucent yellow-green, nearest to RHS 145B; finely veined green, nearest to RHS 143A and 143B.

Inflorescence: To date, 'PHELST01' has not flowered.

COMPARISONS WITH THE PARENT PLANTS

Plants of the new cultivar 'PHELST01' differ from the parent, an unnamed *Philodendron bipinnatifidum* plant that typifies the species, in the characteristics described in Table 1 below.

TABLE 1

| Characteristic | 'PHELST01' | The parent plant. |
|---|---|---|
| Foliage aspect. | Moderately concave; foliar lobes are strongly pendulous. | Carinate, margins slightly revolute. |
| Thickness of foliage. | Thicker than the parent plant. | Thinner than 'PHELST01'. |
| General coloration of the foliage. | Darker green, relative to the mother plant. | Lighter green, relative to 'PHELST01'. |

COMPARISONS WITH THE MOST SIMILAR VARIETY KNOWN TO THE INVENTOR

Plants of the new cultivar 'PHELST01' differ from the most similar cultivar known to the inventor, an unnamed *Philodendron bipinnatifidum* 'Little Hope' U.S. Plant Pat. No. 26,282, in the characteristics described in Table 2 below.

TABLE 2

| Characteristic | 'PHELST01' | 'Little Hope' |
|---|---|---|
| Foliage shape. | Broadly ovate; lobed. | Hastate; lobed. |
| Depth of lobe sinuses. | Shallower than 'Little Hope'. | Deeper than 'PHELST01'. |
| General coloration of the foliage, adaxial surface. | Darker green, relative to 'Little Hope'. | Lighter green, relative to 'PHELST01'. |

TABLE 2-continued

| Characteristic | 'PHELST01' | 'Little Hope' |
|---|---|---|
| General coloration of the foliage, abaxial surface. | Darker green, relative to 'Little Hope'. | Lighter green, relative to 'PHELST01'. |

That which is claimed is:

1. A new and distinct variety of *Philodendron* plant named 'PHELST01', substantially as described and illustrated herein.

* * * * *